(12) United States Patent
Banchieri et al.

(10) Patent No.: US 7,409,039 B2
(45) Date of Patent: *Aug. 5, 2008

(54) X-RAY TECHNIQUE-BASED NONINTRUSIVE INSPECTION APPARATUS

(75) Inventors: Andrew J. Banchieri, Newark, CA (US); David E. Kresse, Walnut Creek, CA (US)

(73) Assignee: GE Homeland Protection, Inc., Newark, CA (US)

( * ) Notice: Subject to any disclaimer, the term of this patent is extended or adjusted under 35 U.S.C. 154(b) by 566 days.

This patent is subject to a terminal disclaimer.

(21) Appl. No.: 10/917,680

(22) Filed: Aug. 12, 2004

(65) Prior Publication Data

US 2005/0013405 A1    Jan. 20, 2005

Related U.S. Application Data

(62) Division of application No. 10/300,472, filed on Nov. 19, 2002, now Pat. No. 6,859,518.

(51) Int. Cl.
*G01N 23/04* (2006.01)
(52) U.S. Cl. .......................... 378/57; 378/196; 378/203
(58) Field of Classification Search .................. 378/4, 378/57, 193, 195, 196, 197, 207, 203
See application file for complete search history.

(56) References Cited

U.S. PATENT DOCUMENTS

| | | | |
|---|---|---|---|
| 4,251,726 A | 2/1981 | Alvarez | 376/159 |
| 5,182,764 A | 1/1993 | Peschmann et al. | 378/57 |
| 5,367,552 A | 11/1994 | Peschmann | 378/57 |
| 6,058,159 A | 5/2000 | Conway et al. | 378/68 |
| 6,430,255 B2 | 8/2002 | Fenkart et al. | 378/57 |
| D474,706 S | 5/2003 | Kresse et al. | D10/106 |
| 6,590,956 B2 * | 7/2003 | Fenkart et al. | 378/57 |
| 6,647,091 B2 | 11/2003 | Fenkart et al. | 378/57 |
| 6,707,875 B2 | 3/2004 | Fenkart et al. | 378/4 |
| 2002/0071516 A1 | 6/2002 | Fenkart et al. | 378/4 |

FOREIGN PATENT DOCUMENTS

WO    WO 01/07899 A1    2/2001

* cited by examiner

*Primary Examiner*—Courtney Thomas
(74) *Attorney, Agent, or Firm*—GE Global Patent Operation; Jonathan E. Thomas

(57) ABSTRACT

A nonintrusive inspection apparatus is described of the kind having a base frame, an elongated shield on the base frame, a conveyor belt passing through the shield which is used for transporting closed containers, and a rotating CT scanner subsystem which is used for scanning the container on the conveyor belt. The CT scanner subsystem is mounted through the shield to the base frame. The shield provides sufficient rigidity for the CT scanner subsystem. A cover is positioned over the CT scanner subsystem, but only over a portion of the shield, thereby allowing for a person on one side of the shield to see a person on an opposite side of the shield.

5 Claims, 3 Drawing Sheets

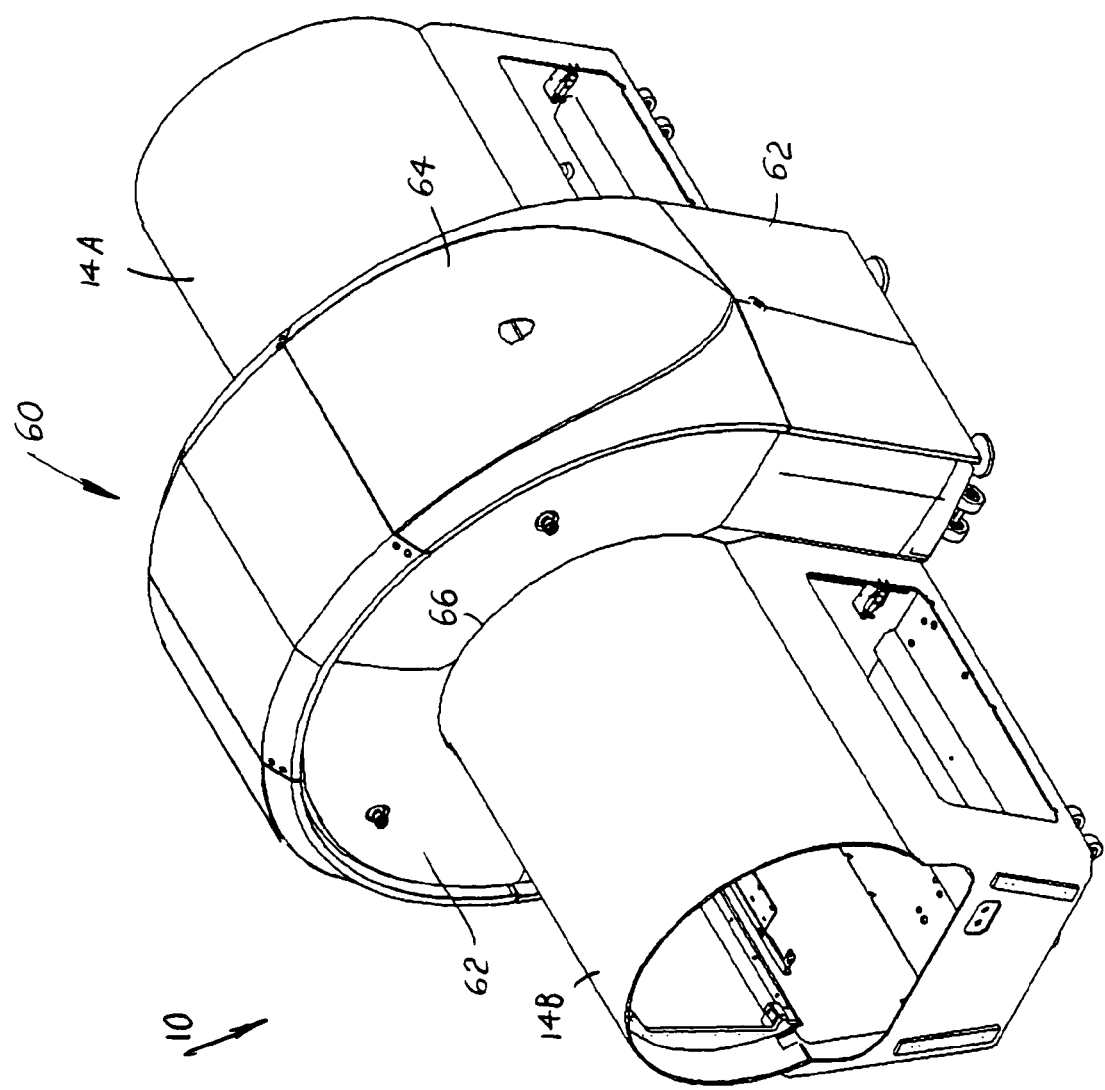

X-RAY TECHNIQUE-BASED NONINTRUSIVE INSPECTION APPARATUS

CROSS-REFERENCE TO OTHER APPLICATIONS

This application is a divisional of U.S. patent application Ser. No. 10/300,472, filed Nov. 19, 2002 now U.S. Pat. No. 6,859,518, entitled, "An X-Ray Technique-Based Nonintrusive Inspection Apparatus".

STATEMENT REGARDING FEDERALLY SPONSORED RESEARCH OR DEVELOPMENT

Certain aspects of this invention were developed with support from the FAA (Federal Aviation Association). The U.S. Government may have rights in certain of these inventions.

BACKGROUND OF THE INVENTION

1). Field of the Invention

This invention relates to an x-ray technique-based nonintrusive inspection apparatus, particularly of the kind that may be used for nonintrusively inspecting closed containers before being loaded into a loading bay of an aircraft.

2). Discussion of Related Art

Inspection apparatus are commonly used for nonintrusively inspecting luggage and other closed containers before being loaded into a loading bay of an aircraft. Older generation inspection apparatus relied merely on conventional x-ray technology for nonintrusively inspecting closed containers. More recently, inspection apparatus which rely on computer tomography (CT) scanning technology have also been utilized. An inspection apparatus utilizing CT scanning technology is described in U.S. Pat. Nos. 5,182,764 and 5,367,552 by Peschmann, et al., which are assigned to the assignee of the present case and which are hereby incorporated by reference.

An inspection apparatus of the aforementioned kind usually has a relatively strong support structure that allows for a CT gantry to be accelerated and decelerated without much distortion in the support structure. The support structure is usually complex and expensive to manufacture. Such an apparatus is also usually intimidating, because it is large and obstructs view and communication between persons standing on opposite sides of such an apparatus.

SUMMARY OF THE INVENTION

The invention provides a nonintrusive inspection apparatus, comprising a base frame, a first shield, a first bearing race, a second bearing race, a gantry, and an x-ray source. The first shield defines a tunnel having a width through which an object can pass. The shield has a length that is at least equal to the width of the tunnel, and is mounted along its length to the base frame. The first bearing race is circumferentially mounted to the shield and through the shield to the base frame. The second bearing race is mounted to the first bearing race for rotation relative to the first bearing race. The gantry is mounted to the second bearing race. The x-ray source is mounted to the gantry.

The system preferably includes a conveyor system, having first and second spaced rollers and a conveyor belt over the rollers, the conveyor belt extending at least partially through the first shield.

The system may also include a channeling structure within the first shield and positioned so that containers entering the first shield on the conveyor belt are moved away from the first shield.

The system may further include a second shield mounted to the base frame on a side of the gantry opposing the first shield, the container moving sequentially through the first shield, the gantry, and the second shield.

The system may further include a cover over at least the gantry and the x-ray source.

The cover may be located over only a portion of the first and second shields.

The cover may include at least one panel which is movable to expose the gantry.

The system may further include a liner on an inner surface of the first shield, of a material different than the first shield, that substantially attenuates x-ray radiation.

The first shield may be made of steel, and the liner may be made of lead.

The first shield may be a circular pipe.

The system may further include a plurality of circular roller members in a space between the first and second bearing races.

According to a further aspect of the invention, a nonintrusive inspection apparatus is provided, comprising a base frame, an elongated first shield, a gantry, an x-ray source, and a cover. The elongated first shield is mounted to the base frame and defines a tunnel through which a container can pass. The gantry is rotatably mounted to the base frame. An x-ray source is mounted to the gantry. The cover is located over the x-ray source, the gantry, and a portion only of the first shield.

The gantry may be mounted through the first shield to the base frame.

The cover may be located over less than 50% of the first shield.

The system may further include an elongated second shield mounted to the base frame on a side of the gantry opposing the first shield, the cover being located over a portion only of the second shield.

BRIEF DESCRIPTION OF THE DRAWINGS

The invention is further described by way of example with reference to the accompanying drawings, wherein:

FIG. 3 is a perspective view of the apparatus.

DETAILED DESCRIPTION OF THE INVENTION

Figure 1:
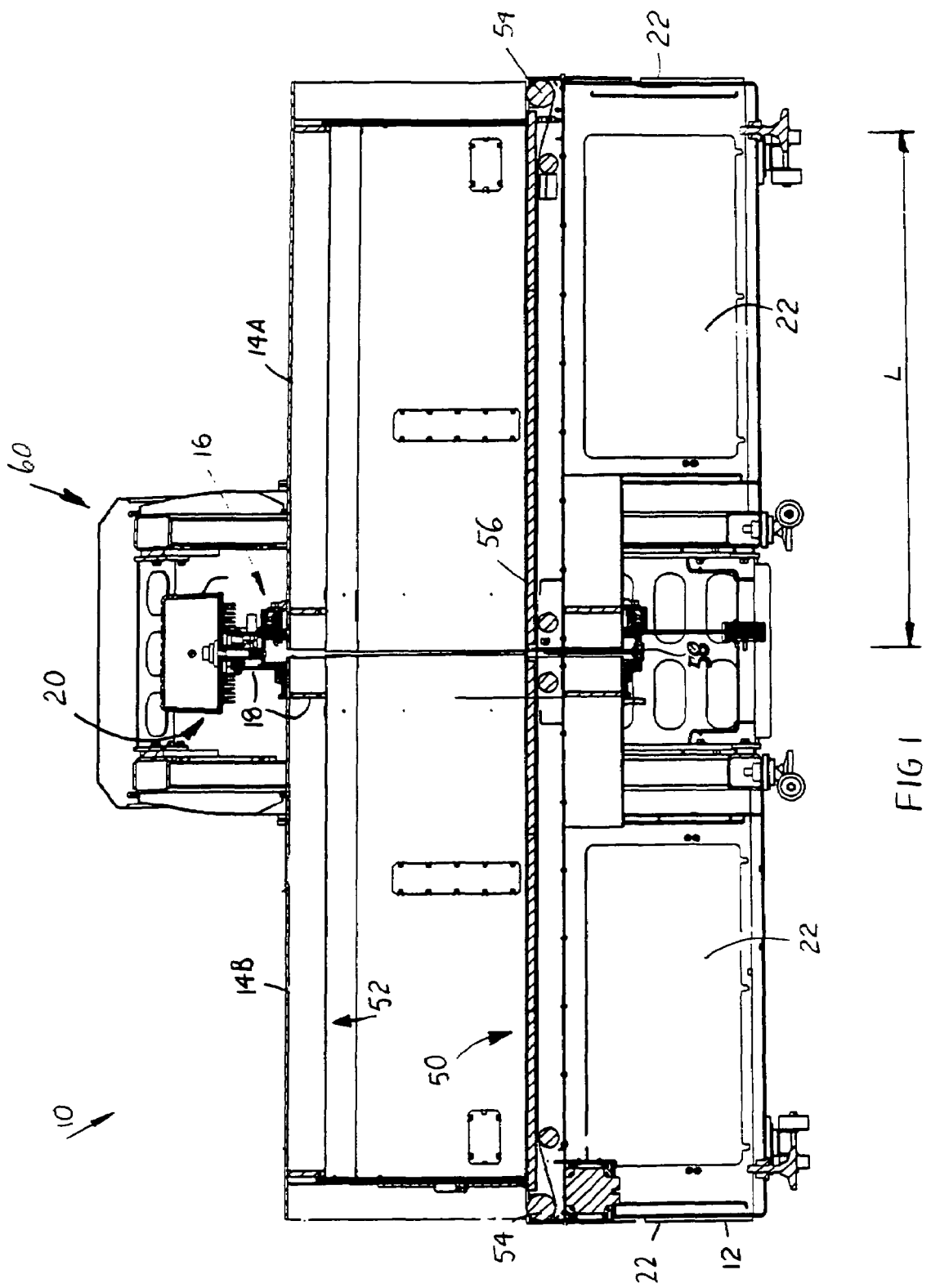
FIG. 1 is a cross-sectional side view illustrating a nonintrusive inspection apparatus according to an embodiment of the invention.

FIG. 1 of the accompanying drawings illustrates a nonintrusive inspection apparatus 10 according to an embodiment of the invention, including a base frame 12, first and second shields 14A and 14B mounted on the base frame 12, a bearing assembly 16 mounted to an end of the first shield 14A, a gantry 18 mounted to the bearing assembly 16, and an x-ray source 20 mounted to the gantry 18.

The base frame 12 is constructed of various panels 22 that together provide a rigid construction. Each shield 14A or 14B is made of a circular pipe having a diameter of 711 mm, a wall thickness of 6.35 mm, and a length L of 2.18 meters. Weld joints secure each shield 14A or 14B along its length L to the base frame 12.

Figure 2:
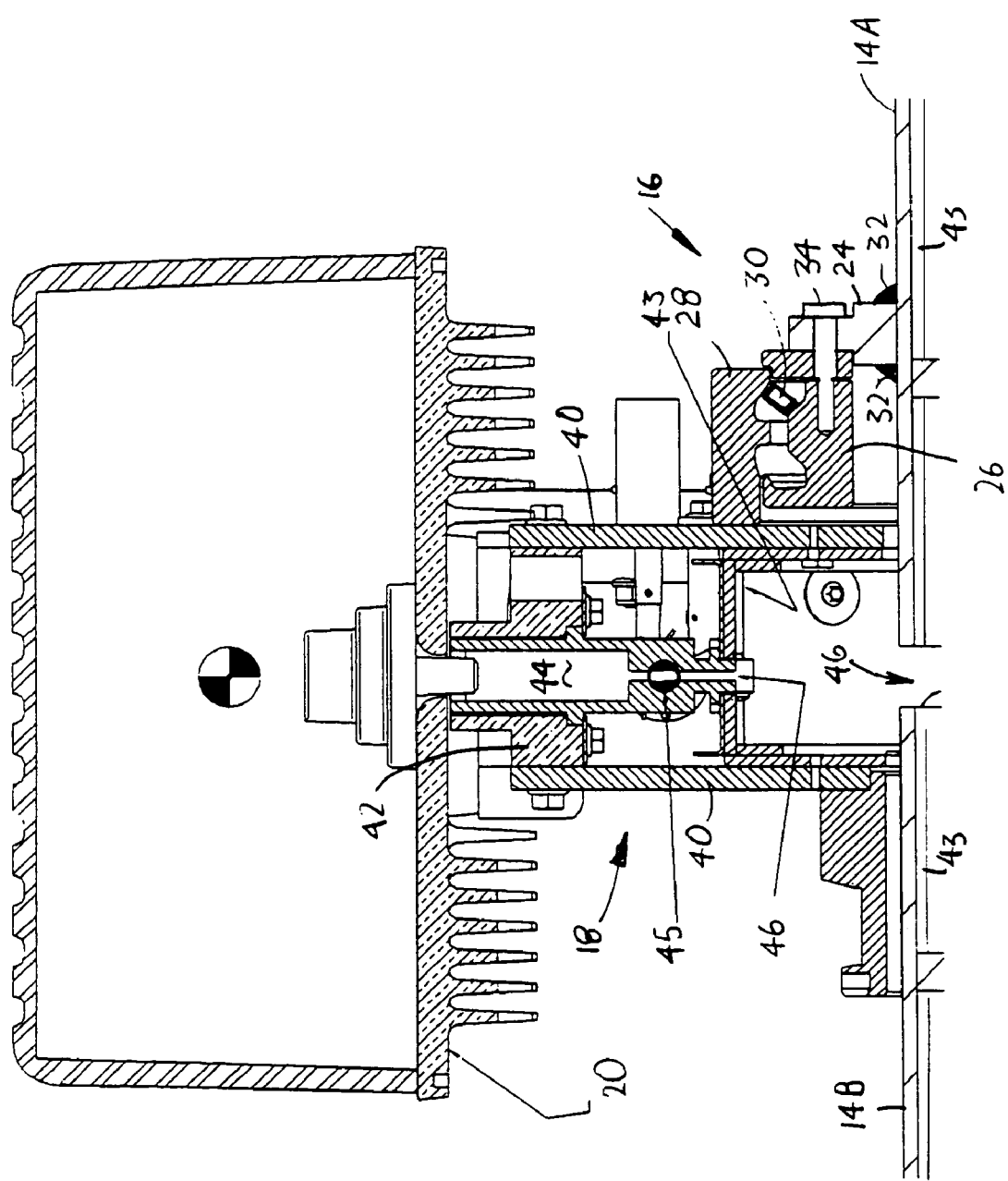
FIG. 2 is an enlarged view of a portion of the apparatus.

Referring to FIG. 2, the bearing assembly 16 includes a flange 24, an inner bearing race 26, an outer bearing race 28, and a plurality of circular roller members 30. The flange 24 has a circular opening which is positioned over a left-hand end of the first shield 14A. The flange 24 is secured to the first shield 14A by means of weld joints 32. The outer bearing race 28 is located around the inner bearing race 26, with the roller members 30 located in a space between the inner and outer bearing races 26 and 28. The roller members 30 align the outer bearing race 28 relative to the inner bearing race 26, while allowing for rotation of the outer bearing race 28 about the inner bearing race 26. The inner bearing race 26 is positioned adjacent to the flange 24 and secured to the flange 24 by means of a number of bolts 34 (one of which is shown).

It can thus be seen that the outer bearing race 28 is mounted for rotation about the first shield 14A. A simple and inexpensive construction is provided by mounting the bearing assembly 16 directly to the first shield 14A. As discussed with reference to FIG. 1, the first shield 14A is also rigidly mounted on top of the base frame 12, in particular because the first shield 14A is welded along its length L to the base frame 12. The first shield 14A thus provides a structure through which the bearing assembly 16 is rigidly mounted to the base frame 12.

The gantry 18 essentially includes opposing gantry plates 40 and interconnection pieces 42. The gantry plates 40 are spaced from one another and secured to one another by the interconnection pieces 42. The gantry plate 40 on the right is located against the outer bearing race 28 and secured thereto. The gantry 18 thus rotates together with the outer bearing race 28. The gantry 18 is typically made of steel and a lead liner 43 is formed on an inner surface thereof, and on inner surfaces of the shields 14A and 14B. The lead liners 43 have the capability to substantially attenuate x-ray radiation.

The x-ray source 20 is mounted to one of the interconnection pieces 42, and thus rotates together with the gantry 18. The x-ray source 20 and the gantry 18 jointly form a rotatable CT scanner subsystem. Power can be provided to the x-ray source 20 so that the x-ray source 20 generates x-rays that are emitted through an x-ray channel 44 and a shutter 45 into the gantry 18 and through a gap 46 between ends of the first and second shield 14A and 14B.

Referring to FIG. 1, the nonintrusive inspection apparatus 10 further includes a conveyor system 50 and a channeling structure 52.

The conveyor system 50 includes conveyor belt rollers 54 and a conveyor belt 56. The conveyor belt rollers 54 are mounted on opposing sides of the base frame 12. The conveyor belt 56 runs over the conveyor belt rollers 54 and a portion thereof is always within the first and second shields 14A and 14B.

The channeling structure 52 includes a number of panels that are positioned within the first and second shields 14A and 14B. These panels are spaced from an inner surface of the first and second shields 14A and 14B.

In use, a container is transferred on the conveyor belt 56 through the second shield 14B and then through the first shield 14A. The channeling structure 52 serves to keep the containers on a central area of the belt 56, and thereby prevents contact between the container and inner surfaces of the shields 14A and 14B. The inner surfaces of the shields 14A and 14B, and in particular the lead liners thereon, are thus protected by the channeling structure 52.

The contents of the container are scanned in x-ray line-scanning mode by transmitting x-rays from the x-ray source 20 through the container and detecting the x-rays with x-ray detectors 58 that are located on the gantry 18 opposing the x-ray source 20. In certain instances it may be required to scan the container in CT mode from opposing sides, in which case the gantry 18, together with the x-ray source 20 and the detectors 58, are rotated on the bearing assembly 16 about the container. The first shield 14A provides a rigid construction that allows for acceleration and braking of the gantry 18 without much movement of a center line of the gantry 18 relative to a center line of the first shield 14A.

In another embodiment, it may be possible for the first shield 14A to be somewhat shorter, without departing from the scope of the invention. The first shield 14A may, for example, have a length that equals its diameter, but preferably has a length that is at least 1.5 times its diameter.

As illustrated in FIGS. 1 and 3, the nonintrusive inspection apparatus further has a cover 60 located over the x-ray source 20, the gantry 18, and portions only of the first and second shields 14A and 14B. The cover 60 includes a number of panels 62 and a door 64 that jointly form an enclosure that seals circumferentially at a periphery 66 on each shield 14A and 14B. The door 64 can be opened to expose the gantry 18 and the x-ray source 20. The cover 60 is located over approximately 0.50 meters of each shield 14A or 14B, so that a circular outer surface of approximately 1.67 meters of each shield 14A or 14B is exposed. In another embodiment, the cover 60 may enclose a larger portion of each shield 14A and 14B, but preferably less than 50% of each shield 14A or 14B.

The cover 60 serves to protect the rotating components, including the x-ray source 20 and the gantry 18, and prevents persons from being injured by these rotating components. However, by locating the cover 60 over only portions of the shields 14A and 14B, a smaller system is provided. The shields 14A and 14B are only approximately 50 inches off the ground, which means that a person on one side of, for example, the shield 14B, can still see the head of a person standing on an opposite side of the shield 14B. The cover 60 thus allows for communication between persons on opposite sides of the system 10, at least across the exposed portions of the shields 14A and 14B, while still protecting the persons from the rotating parts of the system 10.

While certain exemplary embodiments have been described and shown in the accompanying drawings, it is to be understood that such embodiments are merely illustrative and not restrictive of the current invention, and that this invention is not restricted to the specific constructions and arrangements shown and described since modifications may occur to those ordinarily skilled in the art.

What is claimed:

1. A nonintrusive inspection apparatus, comprising:
    a base frame;
    an elongated first shield mounted to the base frame and defining a tunnel through which a container can pass;
    a gantry rotatably mounted to the base frame;
    an x-ray source mounted to the gantry; and
    a cover located over the x-ray source, the gantry and a portion only of the first shield.

2. The system of claim 1, wherein the gantry is mounted through the first shield to the base frame.

3. The system of claim 1, wherein the cover is located over less than 50% of the first shield.

4. The system of claim 1, further comprising:
    an elongated second shield mounted to the base frame on a side of the gantry opposing the first shield, the cover being located over a portion only of the second shield.

5. The system of claim 4, wherein the cover includes left and right portions, at least one of which is movable relative to the other to expose the gantry.

* * * * *